United States Patent [19]

Ito et al.

[11] Patent Number: 5,412,105
[45] Date of Patent: May 2, 1995

[54] THIOPHENE-SILOLE COPOLYMER AND ITS METHOD OF MANUFACTURE

[75] Inventors: Yoshihiko Ito; Kohei Tamao; Shigehiro Yamaguchi, all of Kyoto; Yoshiki Nakagawa, Nishinomiya, all of Japan

[73] Assignee: Shin-Etsu Chemical Co., Ltd., Tokyo, Japan

[21] Appl. No.: 31,980

[22] Filed: Mar. 16, 1993

[30] Foreign Application Priority Data

Jun. 29, 1992 [JP] Japan ................... 4-196609

[51] Int. Cl.$^6$ .............. C07D 333/50; C07D 409/00; C07F 7/08; C08G 77/22
[52] U.S. Cl. ........................... 549/4; 549/59; 556/406; 556/427; 528/30
[58] Field of Search .............. 549/4, 59; 556/406, 556/427; 528/30

[56] References Cited

U.S. PATENT DOCUMENTS

| 2,640,818 | 6/1953 | Di Giorgio | 549/4 |
| 4,691,005 | 9/1987 | Sato et al. | 549/59 |
| 5,059,695 | 10/1991 | Tour et al. | 549/4 |
| 5,143,993 | 9/1992 | Tour et al. | 549/4 |

FOREIGN PATENT DOCUMENTS 0437769 7/1974 U.S.S.R. .

OTHER PUBLICATIONS

Chemical Abstract, CA117(2):8610d, Thiophene-silole Cooligomers and Copolymers, Tamao; Yamaguchi; Shiozaki; Nakagawa and Ito, Jul. 1992.
*Brief Report for the 63rd Spring Conference of the Japanese Chemical Society 1992,* p. 133 (Mar. 16, 1992).

*Primary Examiner*—Glennon H. Hollrah
*Assistant Examiner*—Deborah Lambkin
*Attorney, Agent, or Firm*—Millen, White, Zelano & Branigan

[57] ABSTRACT

A thiophene-silole copolymer represented by the formula below and its method of manufacture are disclosed;

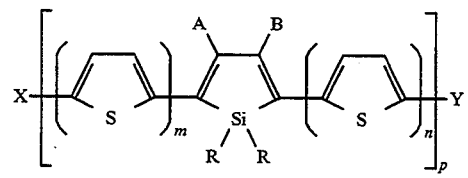

wherein, R is a monofunctional hydrocarbon group having 1 to 20 carbon atoms or hydrogen, A and B are alkyl groups, aromatic groups, alkenyl groups, or represent an aliphatic group forming a ring wherein A is bonded to B, m and p are integers no less than 1, n is a natural number which can be 0, X is a hydrogen or halogen atom, and Y is a hydrogen atom, halogen atom or thiophene.

6 Claims, No Drawings

THIOPHENE-SILOLE COPOLYMER AND ITS METHOD OF MANUFACTURE

FIELD OF THE INVENTION

This invention relates to a thiophene copolymer, which is an organic compound having a $\pi$ electron conjugation system, and its method of manufacture. More particularly, it relates to a novel thiophene-silole copolymer having a light absorption band in the visible region, and its method of manufacture.

BACKGROUND OF THE INVENTION

Some fairly stable organic compounds having a $\pi$ electron conjugation system, such as polyacetylenes, polythiophenes and polypyrroles, have been reported. Recently, apart from homopolymers, copolymers of this type have also been synthesized such as those obtained from thiophene and pyridine, and as they have a unique UV absorption spectrum due to their intramolecular electron donor-acceptor structure, it is hoped that they will find application as new functional materials.

The silole skeleton, on the other hand, is a structure which can function as either an electron donor or an electron acceptor, and although investigations have been made with a view to applying it to polymers, the studies carried out to date have been inadequate.

The Inventors attempted to introduce the silole skeleton into polythiophenes, and thereby discovered a stable thiophene-silole copolymer having a light absorption band in the visible region.

SUMMARY OF THE INVENTION

A first object of the invention to provide a novel thiophene-silole copolymer which could be applied to optical functional materials.

It is a second object of the invention to provide a method of manufacturing a novel thiophene-silole copolymer.

The aforesaid objects are attained by a thiophene-silole copolymer represented by the formula (1) below:

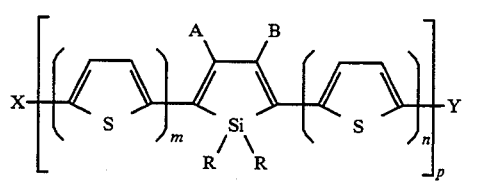

(1)

and by its method of manufacture.

In the formula (1), R is a monofunctional hydrocarbon group having 1 to 20 carbon atoms or hydrogen, A and B are alkyl groups, aromatic groups, alkenyl groups, or represent an aliphatic group forming a ring wherein A is bonded to B, m and p are integers no less than 1, n is a natural number which can be 0, X is a hydrogen or halogen atom, and Y is a hydrogen atom, halogen atom or thiophene.

DETAILED DESCRIPTION OF THE INVENTION

The thiophene-silole copolymer of this invention can easily be obtained by reaction of the compound represented by the general structural formula (2), and the compound represented by the general structural formula (3), in the presence of a nickel or palladium metal complex.

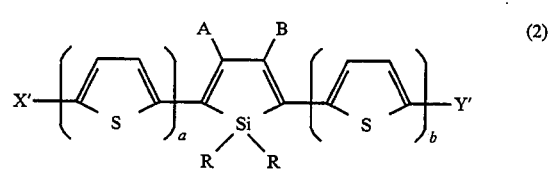

(2)

In the formula (2), R, A and B have identical meanings to those in formula (1), X' is a halogen atom, and Y' is a halogen atom or hydrogen. a and b are natural numbers which can be 0.

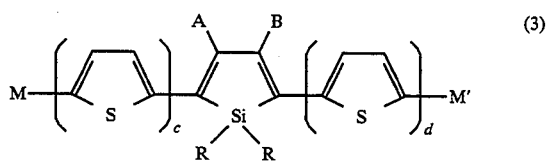

(3)

In the formula (3), R, A and B have identical meanings to those in formula (1), M is $SnR_3$, $BX_2$ such as $B(OH)_2$, MgX or ZnX, and M' is $SnR_3$, $BX_2$ such as $B(OH)_2$, MgX, ZnX or hydrogen, c and d are natural numbers which can be 0. $m=a+c$, and $n=b+d$.

Examples of R in the aforesaid general formula are alkyl groups such as methyl, ethyl, propyl, hexyl, phenyl, tolyl, naphthyl, vinyl and 3,3,3-trifluoropropyl.

From the viewpoint of ease of synthesis, A and/or B preferably contain a functional group such as alcohol, ester, amide or amine. From the viewpoint of obtaining a copolymer according to this invention which has good solubility, it is particularly preferable that A and/or B contain an aliphatic group.

If A and B are bonded together in a 5-membered ring, a copolymer having particularly excellent properties is obtained.

A specific example of such a compound may for example be represented by the formula (4) below:

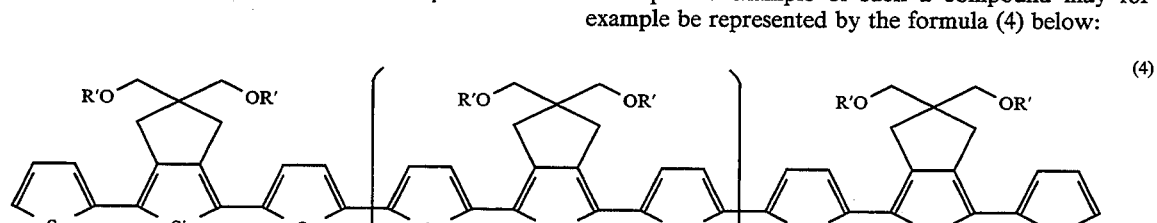

(4)

wherein R is identical to the R of formula (1), R' is a monofunctional organic group having 1-12 carbon atoms, or a silicon group substituted by an organic group, and n' is a natural number which can be 0.

The halogen in the general formulae may typically be chlorine, bromine or iodine, but from the viewpoint of ease of handling and reactivity, bromine is most preferred.

M mentioned hereinbefore is a trisubstituted tin group which may typically be trimethylstannyl, tributylstannyl, or triphenylstannyl.

The compound having the aforesaid formula (4) may easily be obtained by treating the corresponding 2,5-dithienylsilole with N-bromosuccinimide so as to obtain the brominated compound represented by the formula (5) below, and then reacting the brominated compound with the product represented by the formula (6) below.

This compound is obtained by the known method of treating 2, 5-dithienylsilole with n-butyllithium, and then adding a trialkyltin chloride or the like.

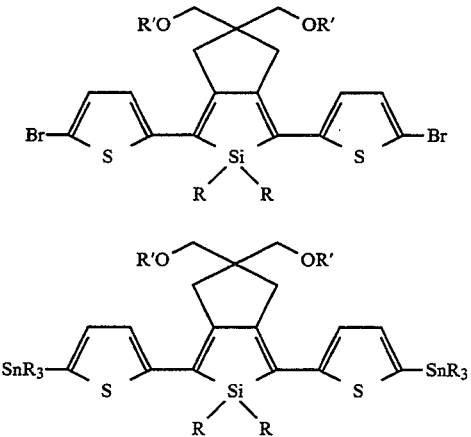

The palladium or nickel metal complex is an indispensable catalyst for obtaining the aforesaid compound (1) of the invention, examples being compounds represented by the general formula $X_2M(PR^1_3)_2$, $X_2M(R^2_2PQPR^3_2)$ or the like, wherein M is Pd or Ni, X is Cl, Br or I, and $R^1$, $R^2$, $R^3$ are alkyl or aryl such as phenyl or substituted phenyl.

Examples of the former include $Cl_2Pd(PMe_3)_2$, $Cl_2Pd(PEt_3)_2$, $Cl_2Pd(PBu_3)_2$, $Cl_2Pd(PPh_3)_2$, $Cl_2Pd(P(OMe)_3)_2$, $Cl_2Pd(P(OEt)_3)_2$; $Cl_2Ni(PMe_3)_2$, $Cl_2Ni(PEt_3)_2$, $Cl_2Ni(PBu_3)_2$, $Cl_2Ni(PPh_3)_2$, $Br_2Ni(PPh_3)_2$, $I_2Ni(PPh_3)_2$, $Cl_2Ni(P(OMe)_3)_2$, $Cl_2Ni(P(OEt)_3)_2$.

Examples of the latter which has divalent ligands include $Cl_2Pd(Ph_2P(CH_2)_4PPh_2)$, $Cl_2Pd(Ph_2P(CH_2)_3PPh_2)$, $Cl_2Pd(1,1'$-bis(diphenylphosphino)ferrocene), $Cl_2Ni(Ph_2P(CH_2)_3PPh_2)$, $Cl_2Ni(Ph_2P(CH_2)_4PPh_2)$.

Other examples include $Pd(PPh_3)_4$, $(PhCH_2)PdCl(PR^1_3)_2$, $Cl_2Pd$ $(MeCN)_2$, $Cl_2Pd(PhCN)_2$, $Cl_2Pd(MeCN)PR_3$, $Cl_2Pd(PhCN)PR_3$, $(Pd(\pi-C_3H_3)Cl)_3$, $Ni(acac)_2$.

A combination use of $PdCl_2$, $Pd(OAc)_2$ or $Pd_2(DBA)_4$ with $R^3P$ or $R^2_2PQPR^3_2$ is also effective. In addition, $Ph_3As$ can also be used.

In the aforesaid formulae, Me is methyl, Et is ethyl, Bu is butyl, Ph is phenyl, acac is acetylacetonate, and DBA is dibenzalacetone.

In order to prepare film, it is desired that the p of the aforementioned formula(l) is larger than 7.

Comparing the oligomer obtained in this invention with polythiophene oligomer confirms that the introduction of one silole ring causes a shift of the UV absorption spectrum towards longer wavelength of the same order as 3 thiophene rings. This is due to the fact that the copolymer of this invention is a combination of thiophene which has electron donor properties, with silole which has electron acceptor properties.

The novel compound of this invention has a light absorption band in the visible region due to characteristic interactions of the $\pi$ electron system, and it can therefore be expected to have application in optical functional materials.

The novel copolymer of this invention has a unique light absorption band in the visible region, and it therefore shows promise as a future optical functional material such as, for example, a light responsive material or an energy storing material.

EXAMPLES

The invention will now be described in more detail with reference to specific examples, but it should be understood that it is no way limited to these examples. In the compounds having the formulae (7)–(12), Me is methyl and Ph is phenyl, and in the compound having the formula (11), Bu is $C_4H_9$.

Synthesis Example 1

1.45 g of the 2,5-dithienylsilole represented by the structural formula (7) below (abbreviated hereafter as TST) and 40 ml of tetrahydrofuran were introduced in a 200 ml flask equipped with a condenser, dropping funnel and stirrer, and 20 ml of a dimethylformamide solution of 0.85 g of N-bromosuccinimide were dripped into the flask.

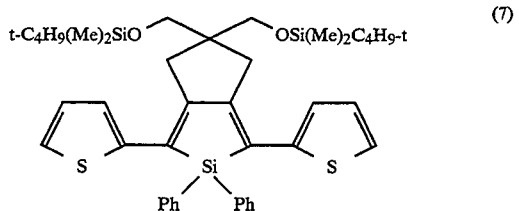

10 minutes after dripping in the dimethylformamide solution, 100 ml water was introduced, and after the reaction was complete, the product was extracted 3 times with 100 ml hexane. The organic layer was collected, washed with water and aqueous sodium chloride, and dried over sodium sulfate.

After distilling off the solvent, 1.2 g of the dibromide represented by the formula (8) below was obtained by silica gel column chromatography (eluent: hexane/methylene chloride=10/1, Rf=0.38).

The bromide thus obtained consisted of yellow crystals having a melting point of 145°–147° C. An elemental analysis showed C=55.36% and H=6.02%, which agreed well with the calculated values of 55.64% and 5.92% respectively for the formula $C_{41}H_{52}O_2S_2Si_3Br_2$.

The $\delta$ values of $^1$HNMR (200 MHz, CDCl$_3$ solvent) were 0.03(s, 12H), 0.89(s, 18H), 2.59(s, 4H), 3.56(s, 4H), 6.52(d, J=3.9 Hz, 2H), 6.81(d, J=3.9 Hz, 2H), 7.10–7.50(m, 6H), 7.60–7.70(m, 4H); and the results $\delta$ of $^{13}$CNMR(50 MHz, CDCl$_3$ solvent) were 5.46, 18.34, 25.94, 36.02, 52.66, 65.45, 111.46, 124.23, 126.21, 128.40, 130.14, 130.47, 131.61, 135.79, 144.63 and 158.64.

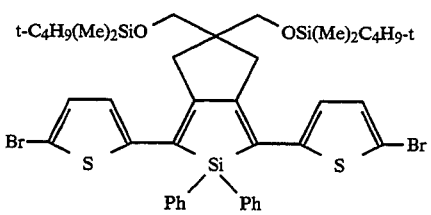

(8)

The TST was synthesized in the following manner.

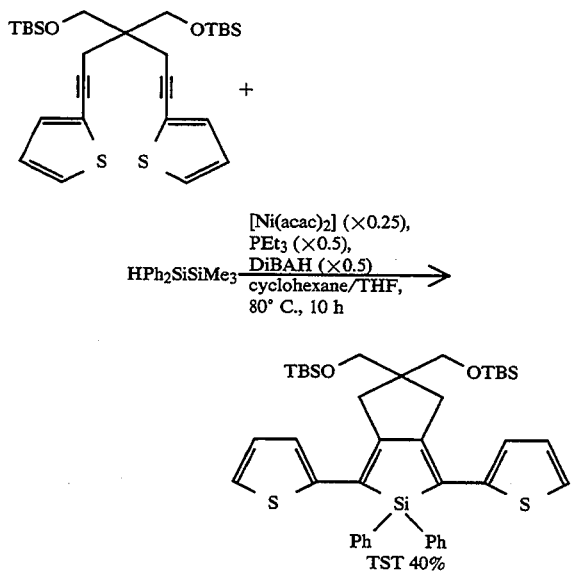

Wherein, TBSO represents t—$C_4H_9(Me)_2SiO$ and OTBS represents $OSi(Me)_2C_4H_9$—t, respectively.

Synthesis Example 2

81 mg of dithienylsilole having the structural formula (9) below was produced in the same way as in Synthesis example 1, except that the amount of N-bromosuccinimide used was 1 equivalent. 120 μl of a 1.67 molar hexane solution of n-butyllithium was added to a dry ether solution of the dithienylsilole at −70° C.

After stirring at −70° C. for 1 hour, 60 μl of tributyl-tin chloride was introduced, and the mixture stirred for a further 1 hour as it was returned to room temperature.

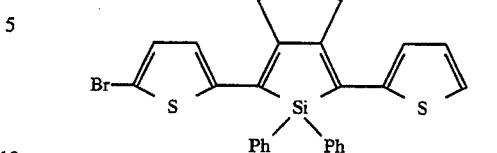

(9)

After obtaining the aforesaid dispersion, 4 ml of a dry tetrahydrofuran solution of 86 mg of a dithienylsilole having the aforesaid formula (9) and 4 μg of $Cl_2Pd(PPh_3)_2$ were added.

The resulting mixture was heated to 65° C., stirred for 5 days, and then filtered over celite.

The filtrate was concentrated, and passed through a silica gel column (eluent: hexane/methylene chloride=3/1) so as to obtain 109 mg of a compound having the formula (10) below.

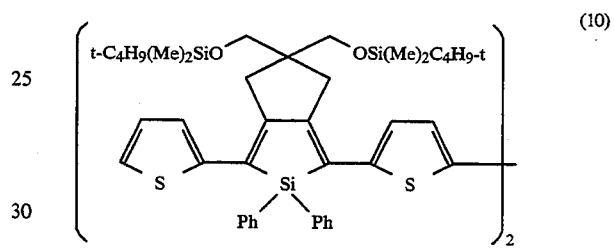

The UV-visible absorption spectrum of the compound obtained showed a maximum absorption at a wavelength of 505 nm.

An elemental analysis showed C=67.71% and H=7.29%, which agreed well with the calculated values of 67.81% and 7.36% respectively for the formula $C_{82}H_{106}O_4S_4Si_6$.

The δ values of $^1$HNMR (200 MHz, CDCl$_3$ solvent) were 0.03(s, 24H), 0.90(s, 36H), 2.68(br.s, 8H), 3.60(s, 8H), 6.68(d, J=3.9 Hz, 2H), 6.82(dd, J=1.0 and 3.7 Hz, 2H), 6.89(d, J=3.9 Hz, 2H), 6.89(dd, J=3.7 and 5.1 Hz, 2H), 7.18(dd, J=1.0 and 5.1 Hz, 2H), 7.30–7.48(m, 12H), 7.64–7.74(m, 8H); and the results δ of $^{13}$CNMR (50 MHz, CDCl$_3$ solvent) were −5.42, 18.37, 25.97, 36.34, 52.66, 65.47, 123.17, 124.07, 124.55, 127.21, 127.81, 128.34, 130.33, 132.10, 135.92, 136.42, 137.87, 142.34 and 158.48.

Synthesis Example 3

A compound having the formula (11) below was obtained by reacting the compounds (9) and (8) in a ratio of 2/1 according to the same method as that of Synthesis example 2.

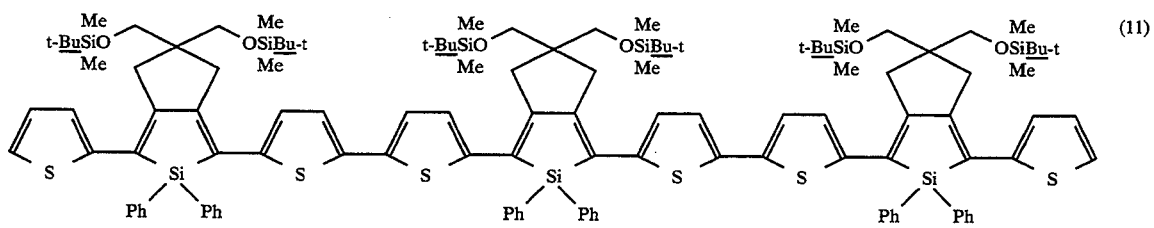

The UV-visible absorption spectrum of the compound obtained showed a maximum absorption at a wavelength of 549 nm.

An elemental analysis showed C=67.58% and H=7.33%, which agreed well with the calculated values of 67.84% and 7.31% respectively for the formula $C_{120}H_{158}S_6O_6Si_9$.

The δ values of $^1$HNMR (200 MHz, CDCl$_3$ solvent) were 0.02(s, 36H), 0.89(s, 54H), 2.67(br.s, 12H), 3.59(br.s, 12H), 6.67(d, J=3.9 Hz, 4H), 6.81(br.d, J=2.7 Hz, 2H), 6.83–6.86(m, 6H), 7.18(dd, J=1.0 and 5.1 Hz, 2H), 7.28–7.48(m, 18H), 7.64–7.74(m, 12H); and the results δ of $^{13}$CNMR(50 MHz, CDCl$_3$ solvent) were −5.41, 18.36, 25.97, 36.25, 52.55, 65.40, 123.61, 124.27, 124.37, 124.64, 127.26, 127.36, 127.41, 128.28, 132.11, 132.19, 135.93, 136.79, 142.15, 143.10 and 158.36.

Synthesis Example 4

0.4 ml of N,N,N',N'-tetramethylethylenediamine and 1.6 ml of a 1.67 molar hexane solution of n-butyllithium were successively added to a dry hexane solution of 495 mg of Me unsubstituted dithienylsilole used in Synthesis example 1, and the mixture stirred for 1 hour. Next, 0.81 ml of tributyltin chloride were dripped in and the mixture stirred for a further hour, then 12 ml of a dry tetrahydrofuran solution of 602 mg of the dibromide obtained in Synthesis example 1 (compound 8) and 52 mg of Cl$_2$Pd(PPh$_3$)$_2$ were added.

The reaction mixture was stirred at 65° C. for 1 week, and after distilling off the solvent, the residue was dissolved in 50 ml chloroform. This chloroform solution was washed twice with a 27 millimolar aqueous solution of potassium cyanide, twice with water, and dried over sodium sulfate. After filtration and distilling off the solvent, the solid residue was dissolved in a small amount of chloroform, reprecipitated with hexane, filtered, and washed with hexane to give 650 mg of the deep red-violet polymer represented by the formula (12) below.

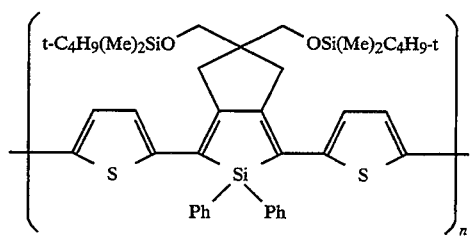
(12)

The weight average molecular weight of this compound was 12,600, and its number average molecular weight was 7,700.

The UV-visible absorption spectrum of the compound obtained showed extremely high absorption at wavelengths of 594 nm and 615 nm.

An elemental analysis showed C=64.61% and H=7.03%, which agreed well with the calculated values of 67.90% and 7.23% respectively for the formula $(C_{41}H_{52}O_2S_2Si_3)_n$ and of 66.50% and 7.23% respectively for the formula $(C_4H_9)_3Sn(C_{41}H_{52}O_2S_2Si_3)_{10}Br$.

The δ values of $^1$HNMR (200 MHz, CDCl$_3$ solvent) were 0.03(s, 12H), 0.89(s, 18H), 2.67(s, 4H), 3.59(s, 4H), 6.78(br.d, J=3.7 Hz, 2H), 6.88(br. d, J=3.7 Hz, 2H), 7.30–7.48(m, 6H), 7.64–7.76(m, 4H); and the results δ of $^{13}$CNMR(50 MHz, CDCl$_3$ solvent) were −5.43, 18.34, 25.95, 36.31, 52.61, 65.33, 123.62, 124.42, 127.42, 128.30, 130.26, 132.04, 135.87, 136.82, 142.10 and 158.34.

Example 1

A nickel catalyst solution was prepared as follows: To a solution of Ni(acac)$_2$(35 mg; 0.138 mmol) in THF(1 mL) were added succesively PEt$_3$(41 μl; 0.276 mmol) and DIBAH(1M solution in hexane, 0.28 mL; 0.28mmol) at room temperature and the mixture was stirred for 0.5 hour.

To a mixture of diyne shown below, disilane HMe$_2$-SiSiMe$_2$H(33 mg; 0.276mmol) and dry THF(3 mL) was added dropwise the nickel solution prepared above at room temperature.

The mixture was refluxed with stirring for 17 hours.

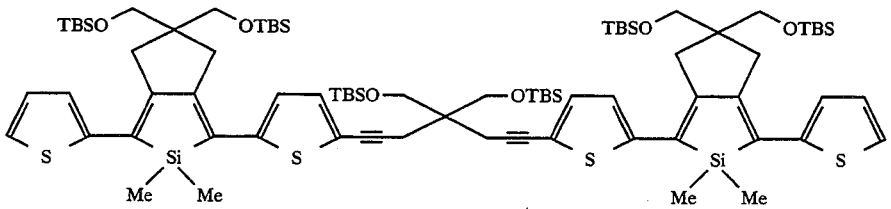

Purification by MPLC on silica gel(hexane/CH$_2$Cl$_2$=5/1, Rf=0.41) gave 92 mg of TS'—TS'—TS'—T (56 μmol, 41% yield) as red purple solid. Maximum UV absorption wavelength of the obtained oligomer was shown in Table 1.

Examples 2–5

H(—TS' T—)11H (Example 2), H(—TTS'T—)27H (Example 3), H(—TTS'TT—)41H (Example 4) and H(—TST—)11H (Example 5) were synthesized by applying the aforesaid methods of synthesis respectively, and their molecular weight, maximum UV absorption wavelength and electrical conductivity after doping with iodine until the electrical conductivity was constant, were measured. The results are shown in Table 1.

The aforementioned T represents thiophene, S and S' mean the unit below;

S:

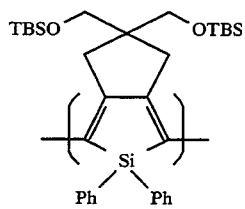

S':

-continued

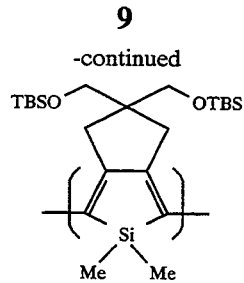

S' can easily be synthesized by nickel-catalyzed intramolecular cyclization of thiophene-containing diyne with dihydrotetramethyldisilane.

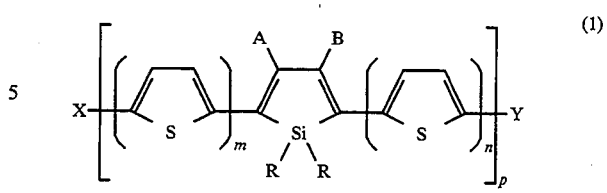

wherein, R is a monofunctional hydrocarbon group having 1 to 20 carbon atoms or hydrogen, A and B are alkyl groups, aromatic groups, alkenyl groups, or represent an aliphatic group forming a ring wherein A is bonded to B, m and p are integers no less than 1, n is a natural number which can be 0, X is a hydrogen or halogen atom, and Y is a hydrogen atom, halogen atom or thiophene.

TABLE 1

| Example | Polymer | Chain strength (n) | Molecular weight | UV Absorption ($\lambda_{max}$) | Conductivity after $I_2$ doping $\sigma$(S/cm) |
|---|---|---|---|---|---|
| Example 1 | SY-326 (TS')₃T | oligomer | | 544 nm 582 nm | |
| Example 2 | SY-289 (TS'T)ₙ | 24 | $M_w = 25.7 \times 10^3$ $M_n = 14.7 \times 10^3$ $M_w/M_n = 1.75$ | 576 nm 618 nm | 0.13 |
| Example 3 | SY-451 (TTS'T)ₙ | 27 | $M_w = 36.3 \times 10^3$ $M_n = 18.4 \times 10^3$ $M_w/M_n = 1.97$ | 546 nm | 0.10 |
| Example 4 | SY-506 (TTS'TT)ₙ | 41 | $M_w = 69.4 \times 10^3$ $M_n = 31.7 \times 10^3$ $M_w/M_n = 2.19$ | 549 nm | 2.4 |
| Example 5 | SY-135 (TST)ₙ | 11 | $M_w = 12.6 \times 10^3$ $M_n = 7.7 \times 10^3$ $M_w/M_n = 1.64$ | 594 nm 615 nm | 0.009 |

What is claimed is:

1. A thiophene-silole copolymer represented by the formula(1) below;

2. A thiophene-silole copolymer claimed in claim 1, wherein R is a group selected from a methyl, ethyl, propyl, hexyl, phenyl, tolyl, naphthyl, vinyl, or 3,3,3-trifluoropropyl.

3. A thiophene-silole copolymer claimed in claim 2, wherein R is a methyl group or phenyl group.

4. A thiophene-silole copolymer claimed in claim 1, wherein A and B are bonded together in a 5-membered ring.

5. A thiophene-silole copolymer claimed in claim 1, wherein p is integers larger than 7.

6. A thiophene-silole copolymer claimed in claim 1, wherein m=1, n=0 and Y is thiophene.

* * * * *